United States Patent
Pflanz et al.

(10) Patent No.: US 11,826,720 B2
(45) Date of Patent: *Nov. 28, 2023

(54) DIATOMACEOUS EARTH COMPOSITION CONTAINING SALT WATER

(71) Applicant: Sartorius Stedim Biotech GmbH, Göttingen (DE)

(72) Inventors: Karl Pflanz, Göttingen (DE); Andreas Pickl, Rosdorf (DE); Florian Hebenstreit, Beberstedt (DE)

(73) Assignee: Sartorius Stedim Biotech GmbH, Gottingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/775,312

(22) PCT Filed: Nov. 6, 2020

(86) PCT No.: PCT/EP2020/081243
§ 371 (c)(1),
(2) Date: May 9, 2022

(87) PCT Pub. No.: WO2021/089760
PCT Pub. Date: May 14, 2021

(65) Prior Publication Data
US 2022/0395807 A1    Dec. 15, 2022

(30) Foreign Application Priority Data
Nov. 7, 2019    (EP) ..................... 19207636

(51) Int. Cl.
| | |
|---|---|
| *B01J 20/02* | (2006.01) |
| *B01J 20/14* | (2006.01) |
| *B01D 37/02* | (2006.01) |
| *B01J 20/04* | (2006.01) |
| *B01J 20/28* | (2006.01) |
| *B01J 20/30* | (2006.01) |
| *C12M 1/00* | (2006.01) |
| *C12N 1/02* | (2006.01) |
| *C12N 5/00* | (2006.01) |

(52) U.S. Cl.
CPC .............. *B01J 20/14* (2013.01); *B01D 37/02* (2013.01); *B01J 20/046* (2013.01); *B01J 20/28004* (2013.01); *B01J 20/28016* (2013.01); *B01J 20/3078* (2013.01); *B01J 20/3092* (2013.01); *C12M 47/10* (2013.01); *C12N 1/02* (2013.01); *C12N 5/0081* (2013.01)

(58) Field of Classification Search
CPC .... B01J 20/14; B01J 20/046; B01J 20/28004; B01D 37/02
See application file for complete search history.

(56) References Cited

FOREIGN PATENT DOCUMENTS

| | | | |
|---|---|---|---|
| CN | 106881065 | 6/2017 | |
| CN | 109012575 | 12/2018 | |
| EP | 3473336 | 4/2019 | |
| EP | 3473336 A1 | 4/2019 | |
| JP | H10118426 A | 5/1998 | |
| WO | 2009/067718 A1 | 5/2009 | |
| WO | WO-2010042614 A1 * | 4/2010 | ............ B01D 15/00 |

OTHER PUBLICATIONS

Bye et al., British J of Industrial Medicine, 1984, 41:228-234.*
Farrah et al., Applied and Environmental Microbiology, 1991, 2502-2506.*
International Search Report and Written Opinion of the International Searching Authority for International Application No. PCT/EP2020/081243, completed Jan. 18, 2021.

* cited by examiner

*Primary Examiner* — Bin Shen
(74) *Attorney, Agent, or Firm* — McDonnell Boehnen Hulbert & Berghoff, LLC

(57) ABSTRACT

The present invention relates to an improved diatomaceous earth composition containing salt water. The diatomaceous earth composition according to the present invention comprises an agglomerated mixture of calcined diatomaceous earth particles, water and at least one inorganic salt, wherein the mass ratio of the calcined diatomaceous earth particles and water is in the range of 1:1.0 to 1:2.0, and wherein the content of the at least one inorganic salt is equal to or more than 0.25 parts by mass based on 100 parts by mass of water. In a further aspect, the present invention relates to a method for producing the diatomaceous earth composition according to the present invention. In another aspect, the present invention relates to the use of the diatomaceous earth composition according to the present invention as an agent for precoat filtration or dynamic body feed filtration in biopharmaceutical applications.

12 Claims, 4 Drawing Sheets

DIATOMACEOUS EARTH COMPOSITION CONTAINING SALT WATER

This application is a national stage application under 35 U.S.C. § 371 of International Application No. PCT/EP2020/081243, filed Nov. 6, 2020, which claims priority to European Patent Application No. 19207636.2, filed Nov. 7, 2019, the disclosures of which are explicitly incorporated by reference herein.

The present invention relates to a diatomaceous earth composition containing salt water. In a further aspect, the present invention relates to a method for producing the diatomaceous earth composition according to the present invention. In another aspect, the present invention relates to the use of the diatomaceous earth composition according to the present invention as an agent for precoat filtration or dynamic body feed filtration in biopharmaceutical applications.

In the biopharmaceutical process, cells which produce a product such as antibodies are usually propagated in fermenters. At the end of the fermentation process, the cells as well as the cell debris have to be separated from the product in order to obtain a clear supernatant with the desired product.

Typically, in order to achieve this separation, centrifugation is performed with subsequent sterile filtration. However, sterile filtration frequently results in blocking of the filter after a certain time, which makes the use of several filters inevitable for the processing of a fermenter. Sterile filtration without prior centrifugation would immediately lead to a blockage of the filter, thereby even making filtration impossible. The entire separation procedure, including centrifugation and sterile filtration, requires a significantly long time and is connected to complicated working steps and thus increased costs.

One way in which the centrifugation step and the blocking of the filter can be circumvented is precoat filtration using diatomaceous earth (DE). For this purpose, diatomaceous earth is added in a certain amount to the cell broth and then filtered. During this precoat filtration, diatomaceous earth builds a coarse-pore filter cake on the sterile filter in which the cells and the cell debris are bound, which can thus no longer contribute to the blockage of the filter. Alternatively, dynamic body feed filtration may be applied.

In brief, diatomaceous earth is a naturally occurring, soft, siliceous sedimentary rock which is composed of the fossilized remains of diatoms, a type of hard-shelled protists, also referred to as chrysophytes. From a chemical perspective, diatomaceous earth is mostly composed of amorphous silica, but also contains a considerable amount of crystalline silica. Depending on its natural deposit and on its further processing such as calcination, diatomaceous earth may contain up to 15 mass % cristobalite and 1 mass % quartz.

For the use of diatomaceous earth in laboratories, the open dosage, e.g. via a funnel, is preferred, since various fermenter shapes and typically multiple samples have to be complied with. On an industrial scale, specifically developed packaging solutions can be used which allow for a mostly dust-free connectivity.

A major problem arising from the use of diatomaceous earth in the laboratory is the extremely high release of dust particles, which particularly occurs when using the dry material which has a powdery morphology. As a result, diatomaceous earth in its pure form is not suitable for working outside of safety workbenches supplied with fume hoods. In particular, due to the considerable amount of crystalline silica in terms of cristobalite and quartz, both of which are highly respirable, the inhalation of dust particles released from diatomaceous earth is harmful to the lungs, causing silicosis. Moreover, crystalline silica has also been presumed to be a carcinogen for humans. In contrast thereto, amorphous silica is considered to have a low toxicity. Nevertheless, the prolonged inhalation thereof may lead to an alteration of the lungs. In addition to the above considerations in view of health issues, the generation of dust results in further problems regarding general hygienic requirements in the working environment.

Attempts to form granulates of diatomaceous earth by using binders do not significantly reduce the release of dust particles, since such granulates also generate dust particles by friction, which are then released when handled in an open manner. Besides, a disadvantage of this approach lies in the binders as such, which are introduced into the sample solution, thereby contaminating the sample and possibly interfering with the subsequent analysis thereof.

Moistening of diatomaceous earth with water reduces the release of dust particles. Furthermore, it allows for an open handling and does not add any new substances to the aqueous sample. Depending on the mass ratio of diatomaceous earth and water, products from crumbly to solid shape are obtained. However, these products are often difficult to handle, since they are no longer free-flowing, in particular when the mass ratio is about 1:3 or even less. Besides, adding large amounts of water to the diatomaceous earth leads to a further undesirable dilution of the sample. A further problem which results from the additional input of water is the promotion of germ growth and the endotoxin formation associated therewith, leading to a contamination of the sample.

In this context, EP 3 473 336 A1 describes that when the moistening of diatomaceous earth with water is optimized, the resulting diatomaceous earth composition exhibits a particularly low release of dust particles. For example, compared to dry diatomaceous earth, a diatomaceous earth composition having a mass ratio of diatomaceous earth and water in the range of 1:1 to 1:2 allows for a reduction of the number of released dust particles by more than 80%, as shown in FIG. 1. Such a diatomaceous earth composition can be handled in an open manner without significant health risks.

Unexpectedly, mixing dry diatomaceous earth and water adversely affects the filtration properties of diatomaceous earth. In particular, wetting of dry diatomaceous earth with water leads to a deterioration of the filtration performance when using the diatomaceous earth composition as an agent for precoat filtration or dynamic body feed filtration in biopharmaceutical applications. Disadvantageously, compared to dry diatomaceous earth, the filtration time required for processing a specific filtration volume increases.

In view of the above, the technical problem underlying the present invention is to provide a diatomaceous earth composition which shall exhibit a significantly reduced release of dust particles, without having the filtration properties of diatomaceous earth, in particular the filtration performance thereof, adversely affected.

The above technical problem is solved by providing the embodiments characterized in the claims.

Specifically, according to the present invention, there is provided a diatomaceous earth composition, comprising an agglomerated mixture of calcined diatomaceous earth particles, water and at least one inorganic salt, wherein the mass ratio of the calcined diatomaceous earth particles and water is in the range of 1:1.0 to 1:2.0, and wherein the content of the at least one inorganic salt is equal to or more than 0.25 parts by mass based on 100 parts by mass of water.

As found by the present inventors, upon wetting with water, the mechanical stability of diatomaceous earth is reduced, and shear forces which occur during the mixing process alter the surface characteristics of the diatomaceous earth particles. Such alteration of the surface characteristics may be seen as the origin of deteriorated filtration performance. Surprisingly, these problems can be overcome by the presence of at least one inorganic salt in the course of mixing dry diatomaceous earth and water.

In particular, due to the presence of at least one inorganic salt, the content of which is equal to or more than 0.25 parts by mass based on 100 parts by mass of water, the diatomaceous earth composition according to the present invention maintains excellent filtration performance, when used as an agent for precoat filtration or dynamic body feed filtration in biopharmaceutical applications, which is comparable to using dry diatomaceous earth. At the same time, the diatomaceous earth composition according to the present invention shows a reduced release of dust particles in comparison with dry diatomaceous earth, thereby allowing for an easy handling and minimizing the risk of inhaling dust particles, since the mass ratio of diatomaceous earth and water is optimized.

As mentioned above, the diatomaceous earth composition according to the present invention comprises an agglomerated mixture of calcined diatomaceous earth particles, water and at least one inorganic salt.

Herein, the diatomaceous earth particles used may be calcined by any method known in the art. Due to the calcination, the diatomaceous earth particles are free of water, yielding dry diatomaceous earth. Thereby, it is possible to precisely adjust the mass ratio of the calcined diatomaceous earth particles and water, since no additional amount of water is added by the calcined diatomaceous earth particles.

In addition, the calcined diatomaceous earth particles are preferably free of organic residues originating from their algae origin. For this purpose, the diatomaceous earth particles may undergo extensive (acidic) washing procedures before and/or after calcination.

Preferably, the water used for the above-defined diatomaceous earth composition is free of endotoxins and free of bacteria, with the latter to be regarded as the source of endotoxins. Thereby, it is possible to easily ensure a low endotoxin content in the diatomaceous earth composition. Accordingly, in a specific embodiment of the present invention, the above-defined diatomaceous earth composition preferably has an endotoxin content of equal to or less than 0.5 EU/mL, as described further below in more detail. Water which is free of endotoxins and free of bacteria can be obtained by γ-sterilization, for instance, as also described further below in more detail.

Wherever applicable in the present application, the term "free of" is not deemed to be construed literally, i.e. it shall rather mean "substantially free of". Accordingly, a tiny amount may be encompassed by the term "free of" as long as it does not adversely affect the advantageous effects of the present invention.

According to the present invention, the mass ratio of the calcined diatomaceous earth particles and water is in the range of 1:1.0 to 1:2.0. Accordingly, by mixing the calcined diatomaceous earth particles and water in the presence of the at least one inorganic salt in the above-mentioned mass ratio, agglomerates are formed which contain the calcined diatomaceous earth particles in an amount of 33.3 to 50.0 mass %, and which contain water in an amount of 50.0 to 66.7 mass %, based on the total mass of the calcined diatomaceous earth particles and water. Furthermore, and as mentioned above, the agglomerates contain equal to or more than 0.25 parts by mass of the at least one inorganic salt based on 100 parts by mass of water.

In a preferred embodiment of the above-defined diatomaceous earth composition, the mass ratio of the calcined diatomaceous earth particles and water is in the range of 1:1.1 to 1:1.7. That is, in this preferred embodiment, the agglomerates formed contain the calcined diatomaceous earth particles in an amount of 37.0 to 47.6 mass %, and contain water in an amount of 52.4 to 63.0 mass %, based on the total mass of the calcined diatomaceous earth particles and water. In a more preferred embodiment of the diatomaceous earth composition as defined above, the mass ratio of the calcined diatomaceous earth particles and water is in the range of 1:1.2 to 1:1.4. That is, in this more preferred embodiment, the agglomerates formed contain the calcined diatomaceous earth particles in an amount of 41.7 to 45.5 mass %, and contain water in an amount of 54.5 to 58.3 mass %, based on the total mass of the calcined diatomaceous earth particles and water. In case the mass ratio of the calcined diatomaceous earth particles and water falls within the ranges as defined above, the diatomaceous earth composition according to the present invention, which comprises the calcined diatomaceous earth particles, water and the at least one inorganic salt in form of an agglomerated mixture, exhibits a particularly low release of dust particles.

As mentioned above, according to the present invention, the content of the at least one inorganic salt is equal to or more than 0.25 parts by mass based on 100 parts by mass of water. When the content of the at least one inorganic salt satisfies the above-mentioned lower limit, the surface characteristics of the diatomaceous earth particles are not substantially altered, and excellent filtration performance can be maintained.

In this respect, it is understood that containing 0.25 parts by mass of the at least one inorganic salt based on 100 parts by mass of water means that the content of the at least one inorganic salt in an aqueous solution is 0.25/(100+0.25) mass %, i.e. 0.249 mass %. As recognized by the skilled person, the above values can be easily converted into each other. For the sake of convenience, the corresponding values converted into mass % are given in parentheses hereinafter.

When the at least one inorganic salt is absent or the content thereof is not sufficient, i.e. below the above-mentioned lower limit of 0.25 parts by mass (corresponding to 0.249 mass %), the mechanical stability of the diatomaceous earth particles is reduced, resulting in a deterioration of the filtration performance. The reason therefor lies in the shear forces occurring during the mixing process, which alter the surface characteristics of the diatomaceous earth particles. The content of the at least one inorganic salt based on 100 parts by mass of water is preferably equal to or more than 0.5 parts by mass (corresponding to 0.498 mass %), more preferably equal to or more than 1 part by mass (corresponding to 0.990 mass %), and still more preferably equal to or more than 1.5 parts by mass (corresponding to 1.478 mass %), without, however, being limited thereto.

Regarding the upper limit of the content of the at least one inorganic salt, the present invention is not particularly limited. As long as the at least one inorganic salt is completely soluble in water, the content of the at least one inorganic salt based on 100 parts by mass of water may be equal to or less than 100 parts by mass (corresponding to 50 mass %), equal to or less than 75 parts by mass (corresponding to 42.86 mass %), equal to or less than 50 parts by mass (corresponding to 33.33 mass %), equal to or less than 25 parts by mass (corresponding to 20 mass %), equal to or less than 20 parts by mass (corresponding to 16.67 mass %), equal to or less than 15 parts by mass (corresponding to 13.04 mass %), or equal to or less than 10 parts by mass (corresponding to 9.09 mass %). The content of the at least one inorganic salt may be even such that it corresponds to a saturated solution of the at least one inorganic salt in water, e.g. at 25° C.

However, increasing the content of the at least one inorganic salt beyond 5 parts by mass based on 100 parts by mass of water does not have a further significant impact on the filtration performance, as expressed by the relationship between filtration volume and filtration time. Thus, the content of the at least one inorganic salt based on 100 parts by mass of water is preferably equal to or less than 5 parts by mass (corresponding to 4.76 mass %), more preferably equal to or less than 4 parts by mass (corresponding to 3.85 mass %), still more preferably equal to or less than 3 parts by mass (corresponding to 2.91 mass %), and even more preferably equal to or less than 2 parts by mass (corresponding to 1.96 mass %), without, however, being limited thereto.

For example, without limitation, the content of the at least one inorganic salt based on 100 parts by mass of water may be in the range of 0.25 to 5 parts by mass, 0.5 to 4 parts by mass, 1 to 3 parts by mass, or 1.5 to 2 parts by mass.

When using the diatomaceous earth composition according to the present invention as a filtration aid in a filtration medium, i.e. in a sample to be filtrated, the at least one inorganic salt present in the diatomaceous earth composition is strongly diluted upon contact with the filtration medium, which means that it does not substantially affect the properties thereof. In the filtration process of fermentation and protein solutions, where the presence of externally added salts is particularly undesired, the at least one inorganic salt is typically diluted by a factor of 20. For example, when using a diatomaceous earth composition, where the content of the at least one inorganic salt is 1.8 parts by mass based on 100 parts by mass of water (corresponding to 1.77 mass %), the content of the at least one inorganic salt in the finally obtained filtrate will be only 1.8 parts by mass based on 2000 parts by mass of water (corresponding to 0.0899 mass %), which is unlikely to influence the quality of the filtrate.

As far as the at least one inorganic salt as such is concerned, the present invention is not particularly limited as long as the at least one inorganic salt is sufficiently soluble in water and does not substantially change the pH thereof. In a preferred embodiment of the diatomaceous earth composition as defined above, the at least one inorganic salt is selected from an alkali metal halide, e.g. an alkali metal chloride, an alkaline earth metal halide, e.g. an alkaline earth metal chloride, or mixtures thereof. Among the alkali metal halides, sodium chloride (NaCl) and potassium chloride (KCl) are particularly suitable, without, however, being limited thereto. Among the earth alkaline metal halides, magnesium chloride ($MgCl_2$) and calcium chloride ($CaCl_2$)) are particularly suitable, without, however, being limited thereto. Advantageously, the chlorides of sodium, potassium, magnesium and calcium show excellent solubility in water and are neutral in aqueous solution. Besides, they are non-toxic. As required, they can be used alone or in combination.

Apart from alkali metal halides and earth alkaline metal halides, alkali metal sulfates and earth alkaline metal sulfates can principally be used as well.

As far as the average particle size of the calcined diatomaceous earth particles is concerned, the present invention is not particularly limited. For example, the average particle size may be in the range of 0.1 to 800 µm, e.g. 0.1 to 600 µm, 0.1 to 400 µm, 0.1 to 200 µm or 0.2 to 200 µm, without, however, being limited thereto. In a specific embodiment of the above-defined diatomaceous earth composition, the average particle size of the calcined diatomaceous earth particles is in the range of 0.5 to 10 µm. For adjusting the average particle size, the diatomaceous earth particles as obtained after the calcination may be classified using any mechanical separation procedure known in the art. In case the average particle size of the calcined diatomaceous earth particles falls within the above-defined ranges, an agglomerated mixture can be obtained, wherein the calcined diatomaceous earth particles are sufficiently free-flowing. Herein, the average particle size of the calcined diatomaceous earth particles is measured by laser diffraction (accuracy: ±1%), using a conventional particle sizing instrument (Mastersizer 2000, Malvern Instruments).

In another specific embodiment of the present invention, the diatomaceous earth composition as defined above further comprises a water-impermeable and γ-sterilizable packaging which seals the agglomerated mixture of calcined diatomaceous earth particles, water and at least one inorganic salt, i.e. which encloses the agglomerated mixture in a hermetic manner so that practically no material exchange with the environment can take place.

Due to the water-impermeability of the packaging, it can be ensured that the mass ratio of the calcined diatomaceous earth particles and water is maintained during storage of the above-defined diatomaceous earth composition even over a longer period of time, such as several months up to three years. That is, the diatomaceous earth composition when being packaged is prevented from readily turning back into the dry form which is prone to release dust particles. Advantageously, in case the above-defined diatomaceous earth composition is packaged, it can be easily stored in different quantities and shipped. After removal of the packaging, the desired quantity can be dosed in an almost dust-free manner.

Furthermore, since the packaging is γ-sterilizable, i.e. the packaging itself as well as the content thereof can be sterilized through irradiation with γ-rays, it is possible to obtain an endotoxin content of equal to or less than 0.5 EU/mL in the diatomaceous earth composition, as described further below.

From a chemical perspective, endotoxins are lipopolysaccharides. They are components of gram-negative bacterial cell walls, which are known to induce fever in humans, e.g. when injected into the bloodstream. The presence of endotoxins in the blood, which is also referred to as endotoxemia, leads to septic shocks if the immune response is severely pronounced. Disadvantageously, bacterial endotoxins are heat-stable, and their toxicity is not dependent on the presence of bacterial cells.

Herein, the endotoxin content of the diatomaceous earth composition is measured in accordance with the limulous amoebocyte lysate test, simply abbreviated as LAL test, which is the most common method known in the art for endotoxin testing. In brief, the assay which underlies the LAL test is based on the biology of the horseshoe crab (Limulous) which produces LAL enzymes in blood cells (amoebocytes) to bind and inactivate the endotoxin from invading bacteria. Specifically, LAL serves as a primitive immune system. By inactivating the endotoxin, a clot is formed, which can further protect the horseshoe crab from infection. The LAL test exploits the action of this enzyme, by adding LAL reagent to the sample to be tested, and assaying for clot formation. This can be achieved by optical means as the clot formation renders the sample cloudy. The endotoxin content is specified in terms of a concentration in "endotoxin units" (EU) per volume, e.g. in EU/mL, which approximately corresponds to 0.1 to 0.2 ng endotoxin per milliliter of the sample volume.

As known to the skilled person, endotoxin contents can also be measured using the recombinant Factor C (rFC)-based endotoxin test, which has been approved as an alternative to the conventional LAL test as described above, whilst sparing the endangered horseshoe crabs. The recombinant Factor C-based endotoxin test is endotoxin specific and can eliminate false-positive glucan reactions. Specifically, in the recombinant Factor C-based endotoxin test, the synthetic form of Factor C binds to endotoxins, thereby activating a clotting cascade. Typical rFC-based assays are end-point fluorescence tests, wherein the non-bound Factor C cleaves a fluorogenic substrate, thereby releasing a detectable fluorescent substance.

Herein, the endotoxin content of the diatomaceous earth composition according to the present invention is measured in accordance with the above-described LAL test.

According to the present invention, the endotoxin content of the diatomaceous earth composition as defined above is preferably equal to or less than 0.5 EU/mL, more preferably equal to or less than 0.2 EU/mL, and still more preferably equal to or less than 0.1 EU/mL. Generally, the lower limit of the endotoxin content is not particularly limited according to the present invention. For example, the lower limit may correspond to the lower detection limit of the LAL test, which is about 0.01 EU/mL. Accordingly, a sample having an endotoxin content of 0.01 EU/mL may be considered as being free of endotoxins.

For measuring the endotoxin content, the diatomaceous earth composition according to the present invention is dispersed in 1 L water. Herein, the amount of the diatomaceous earth composition to be dispersed in 1 L water is always such that 40 g of the calcined diatomaceous earth particles are included in the finally obtained dispersion. For example, in case the mass ratio of the calcined diatomaceous earth particles and water is 1:1.0 in the diatomaceous earth composition, 80 g thereof are dispersed in 1 L water, and in case the mass ratio of the calcined diatomaceous earth particles and water is 1:2.0 in the diatomaceous earth composition, 120 g thereof are dispersed in 1 L water. In both of these exemplary cases, the mass of the at least one inorganic salt is not yet included, i.e. it has to be added to the mass of 80 g and 120 g, respectively. In any case, the endotoxin content according to the present invention, measured with the LAL test as described above, is preferably equal to or less than 0.5 EU/mL, more preferably equal to or less than 0.2 EU/mL, and still more preferably equal to or less than 0.1 EU/mL, based on the volume of the finally obtained dispersion. Approximately, this corresponds to an endotoxin content of preferably equal to or less than 12.5 EU/g, more preferably equal to or less than 5 EU/g, and still more preferably equal to or less than 2.5 EU/g, based on the mass of the calcined diatomaceous earth particles, respectively.

In case the diatomaceous earth composition according to the present invention is packaged, the packaging used for sealing the diatomaceous earth composition, which may be a bag or a container, for instance, is not particularly limited as long as it is water-impermeable, in particular impermeable to water vapor, and γ-sterilizable. Typically, laminates composed of different polymeric and metallic layers may be used as the material for the packaging.

In a specific embodiment of the diatomaceous earth composition as defined above, the water-impermeable and γ-sterilizable packaging is composed of a four-layered laminate comprising the following layers (i) to (iv) from the inside to the outside of the packaging, i.e. from the contact side with the agglomerated mixture of calcined diatomaceous earth particles, water and at least one inorganic salt towards the surrounding environment:

(i) a layer of polyethylene (PE) or polypropylene (PP) having a thickness in the range of 30 to 150 µm, preferably in the range of 50 to 120 µm, e.g. 75 µm or 100 µm;

(ii) a layer of polyethylene terephthalate (PET) or oriented polyamide (OPA) having a thickness in the range of 5 to 20 µm, preferably in the range of 8 to 15 µm, e.g. 12 µm;

(iii) a layer of aluminum (ALU) having a thickness in the range of 5 to 20 µm, preferably in the range of 8 to 15 µm, e.g. 12 µm; and (iv) a layer of polyethylene terephthalate (PET) having a thickness in the range of 5 to 20 µm, preferably in the range of 8 to 15 µm, e.g. 12 µm.

In the above-defined four-layered laminate, PE or PP on the inside of the packaging is used as a material for a retort-stable heat sealing layer. The thickness of the PE or PP layer mainly influences the mechanical strength, sealing strength and stiffness of the laminate, being essential for ensuring tight seals. The intermediate PET or OPA layer provides mechanical strength, e.g. puncture resistance and drop resistance, as well as sealing strength, thereby protecting the bond to the ALU layer which is the barrier layer. That is, aluminum is used as a barrier material mainly against oxygen, light and water. Due to the presence of the ALU layer, the four layered-laminate as defined above has a water permeability of at most 0.05 g/m²·day, e.g. at most 0.03 g/m²·day or at most 0.02 g/m²·day, and thus can be considered water-impermeable in the sense of the present invention. Finally, the PET layer on the outside acts as a protecting layer, providing stiffness and tensile strength, and serving as a sealing-resistant substrate for printing of the packaging, as required. Generally, the thicknesses of the four layers (i) to (iv) may be appropriately set with respect to the pouch size, the filling machine, and the mechanical strength and stiffness requirements.

Typical combinations of the above-defined four layers (i) to (iv), which are excellent in water-impermeability, in particular excellent in permeability to water vapor, include PE (100 µm)/PET (12 µm)/ALU (12 µm)/PET (12 µm) as well as PE (75 µm)/OPA (12 µm)/ALU (12 µm)/PET (12 µm), without, however, being limited thereto. The above-mentioned four-layered laminates can be readily exposed to γ-radiation without being damaged, thus allowing for the γ-sterilization of the packaging which seals the agglomerated mixture of calcined diatomaceous earth particles, water and at least one inorganic salt.

In a further aspect, the present invention relates to a method which allows to produce the above-defined diatomaceous earth composition. In this respect, all limitations and definitions provided above for the diatomaceous earth composition according to the present invention equally apply to the method for producing the diatomaceous earth composition according to the present invention, and vice versa.

In particular, the method for producing the diatomaceous earth composition according to the present invention comprises the following steps (a) to (e):

(a) providing calcined diatomaceous earth particles and a solution of at least one inorganic salt in water, wherein the content of the at least one inorganic salt is equal to or more than 0.25 parts by mass based on 100 parts by mass of water;

(b) mixing the calcined diatomaceous earth particles with the solution of at least one inorganic salt in water, wherein the mass ratio of the calcined diatomaceous earth particles and water is in the range of 1:1.0 to 1:2.0, thereby obtaining an agglomerated mixture of calcined diatomaceous earth particles, water and at least one inorganic salt;

(c) optionally sealing the agglomerated mixture of calcined diatomaceous earth particles, water and at least one inorganic salt obtained in step (b) in a water-impermeable and γ-sterilizable packaging, thereby obtaining a sealed agglomerated mixture of calcined diatomaceous earth particles, water and at least one inorganic salt;

(d) optionally sterilizing the sealed agglomerated mixture of calcined diatomaceous earth particles, water and at least one inorganic salt obtained in step (c) by exposure to γ-radiation, thereby obtaining a diatomaceous earth composition with an endotoxin content of equal to or less than 0.5 EU/mL; and (e) optionally removing the packaging from the diatomaceous earth composition obtained in step (c) or (d).

Hereinafter, steps (a) to (e) of the method for producing the diatomaceous earth composition according to the present invention are described in more detail.

In step (a) of the method as defined above, calcined diatomaceous earth particles are provided. As mentioned above, the diatomaceous earth particles which are provided in step (a) have been subject to calcination in advance so as to ensure that they are free of water, thereby allowing for a precise adjustment of the mass ratio in the following step (b). Further, in step (a) of the method as defined above, a solution of at least one inorganic salt in water is provided, wherein the content of the at least one inorganic salt is equal to or more than 0.25 parts by mass based on 100 parts by mass of water. Since the calcined diatomaceous earth particles are free of water, the amount of water included in the diatomaceous earth composition finally obtained by the method for producing the diatomaceous earth composition corresponds to the amount of water provided in step (a) with the solution of at least one inorganic salt in water.

In step (b) of the method as defined above, the calcined diatomaceous earth particles are mixed with the solution of at least one inorganic salt in water, wherein the mass ratio of the calcined diatomaceous earth particles and water is in the range of 1:1.0 to 1:2.0. Thereby, an agglomerated mixture of calcined diatomaceous earth particles, water and at least one inorganic salt is obtained. Upon mixing, the obtained agglomerates contain the calcined diatomaceous earth particles in an amount of 33.3 to 50.0 mass %, and contain water in an amount of 50.0 to 66.7 mass %, based on the total mass of the calcined diatomaceous earth particles and water. Furthermore, the obtained agglomerates contain the at least one inorganic salt such that the content of the at least one inorganic salt is equal to or more than 0.25 parts by mass based on 100 parts by mass of water. In this context, it is assumed that the amount of the at least one inorganic salt included in the diatomaceous earth composition exclusively comes from the solution of at least one inorganic salt in water provided in step (a). As far as the water used for providing the solution in step (a) is concerned, it is preferred that it is free of endotoxins and free of bacteria so as to facilitate the γ-sterilization which is optionally conducted in step (d).

Herein, the mixing of the calcined diatomaceous earth particles and the solution of at least one inorganic salt in water can be conducted by any mixing technique known in the art. In a specific embodiment of the above-defined method, the calcined diatomaceous earth particles and the solution of at least one inorganic salt in water are mixed by spray wetting in step (b). Typically, spray wetting comprises fluidizing the calcined diatomaceous earth particles, and spraying thereonto the solution of at least one inorganic salt in water during the fluidization, resulting in the formation of agglomerates until the desired mass ratio of the calcined diatomaceous earth particles and water is achieved. Alternatively, the calcined diatomaceous earth particles and the solution of at least one inorganic salt in water can be mixed in a conventional mixing machine, e.g. a ploughshare mixer, while stirring. For this purpose, it is preferable to fill the calcined diatomaceous earth particles into the mixing machine before the solution of at least one inorganic salt in water is added. Due to the presence of the at least one inorganic salt, the shear forces which occur during the mixing process do not lead to a substantial alteration of the surface characteristics of the diatomaceous earth particles. That is, regardless of the mixing method applied, it is possible to achieve excellent filtration performance.

In order to prevent the contamination with bacteria, which might lead to the formation of endotoxins, the agglomerated mixture of calcined diatomaceous earth particles, water and at least one inorganic salt obtained in step (b) of the above-defined method may be cooled, e.g. at a temperature of 0° C. to 15° C., 0° C. to 10° C., or 5° C. to 10° C., as required, before optionally carrying out step (c).

In step (c) of the method as defined above, the agglomerated mixture of calcined diatomaceous earth particles, water and at least one inorganic salt which has been obtained in step (b) is optionally sealed in a water-impermeable and γ-sterilizable packaging. Thereby, a sealed agglomerated mixture of calcined diatomaceous earth particles, water and at least one inorganic salt is obtained. Prior to the sealing, the agglomerated mixture obtained in step (b) is transferred into the packaging, which is e.g. a bag or a container, by any means known in the art, typically at room temperature (25° C.). Then, the sealing may be achieved by application of heat, which is also referred to as thermal sealing. However, the present invention is not limited to any specific sealing procedure.

As mentioned above, the packaging is not particularly limited as long as it is water-impermeable, in particular impermeable to water vapor, as well as γ-sterilizable. Furthermore, the packaging provided for sealing the agglomerated mixture of calcined diatomaceous earth particles, water and at least one inorganic salt in step (c) may be for single use or for multiple use, i.e. it may be re-sealable or not.

The sealed agglomerated mixture of calcined diatomaceous earth particles, water and at least one inorganic salt obtained in step (c) of the above-defined method may be cooled in the same manner as explained above in connection with step (b). Thereby, it can be ensured that the sealed agglomerated mixture is not further contaminated with bacteria, which might lead to the formation of endotoxins.

In step (d) of the method as defined above, the sealed agglomerated mixture of calcined diatomaceous earth particles, water and at least one inorganic salt, which has been obtained in step (c), is optionally sterilized by exposure to γ-radiation. Thereby, a diatomaceous earth composition with an endotoxin content of equal to or less than 0.5 EU/mL is obtained.

As known to the skilled person, sterilization of a sample by exposure to γ-radiation is a powerful tool for removing germs, such as bacteria. Since endotoxins are released upon disintegration of gram-negative bacteria, the removal of such bacteria ensures a low endotoxin content in the sterilized sample.

In a specific embodiment of the above-defined method, the dose of the γ-radiation for sterilizing the sealed agglomerated mixture of calcined diatomaceous earth particles, water and at least one inorganic salt in step (d) is in the range of 25 to 100 kGy, e.g. 40 to 80 kGy, 50 to 70 kGy, for example at least 25 kGy, without limitation. Depending on the specific radiation dose which is applied in step (d), the γ-sterilization is conducted for a period ranging from 2 to 10 hours, 3 to 8 hours, or 4 to 6 hours, e.g. 5 hours, without, however, being limited thereto.

Provided that step (d) has been carried out, the diatomaceous earth composition obtained by the above-defined method has a low endotoxin content, i.e. an endotoxin content of preferably equal to or less than 0.5 EU/mL, more preferably equal to or less than 0.2 EU/mL, and still more preferably equal to or less than 0.1 EU/mL, which may be evaluated with the LAL test, as described above. After completion of the γ-sterilization in step (d), the diatomaceous earth composition may be stored at room temperature, i.e. further cooling is not required.

In step (e) of the method as defined above, the packaging which seals the agglomerated mixture of calcined diatomaceous earth particles, water and at least one inorganic salt is optionally removed from the diatomaceous earth composition which has been obtained in step (c), or if carried out, in step (d). Preferably, the packaging is not removed until immediately before use.

In another aspect, the present invention relates to the use of the above-defined diatomaceous earth composition as an agent for precoat filtration or dynamic body feed filtration in biopharmaceutical applications, and specifically relates to the use thereof for precoat filtration or dynamic body feed filtration of eukaryotic and/or prokaryotic cells in an aqueous medium.

When using diatomaceous earth as a filtration aid, it is important to ensure a dust-free application of the diatomaceous earth while maintaining excellent filtration performance. These requirements are fulfilled when using the diatomaceous earth composition according to the present invention.

THE FIGURES SHOW

EXAMPLES

The present invention is further illustrated by the way of the following Examples. However, the present invention is not to be construed as being limited to these Examples.

Diatomaceous earth compositions were obtained by mixing calcined diatomaceous earth particles with ultrapure water or with solutions of at least one inorganic salt in ultrapure water, hereinafter simply referred to as the wetting medium, respectively. In each case, the diatomaceous earth compositions which were obtained by mixing included 4 g of the calcined diatomaceous earth particles and 5 g of water (mass ratio 1:1.25).

The respective diatomaceous earth compositions were then added to 100 mL of a filtration medium comprising Caro Coffee and Ovomaltine (0.60 g Caro Coffee and 0.15 g Ovomaltine per 100 mL water), which imitated the cell broth, to obtain mixtures of the diatomaceous earth composition and the filtration medium. The thus obtained mixtures were then transferred to the funnel of a vacuum filter (Sartolabe® RF 150, filter area: 18 cm$^2$) which was connected to a vacuum pump (Microsarte® e.jet). The filtration started when the respective mixtures in the funnel reached the filter area, and ended when the entire filtration medium passed the filter or when the filter was blocked before the entire filtration medium could pass the filter.

Evaluation was then conducted in terms of filtration performance, i.e. in terms of the relationship between filtration volume and filtration time, which were measured during each filtration run.

Figure 1:
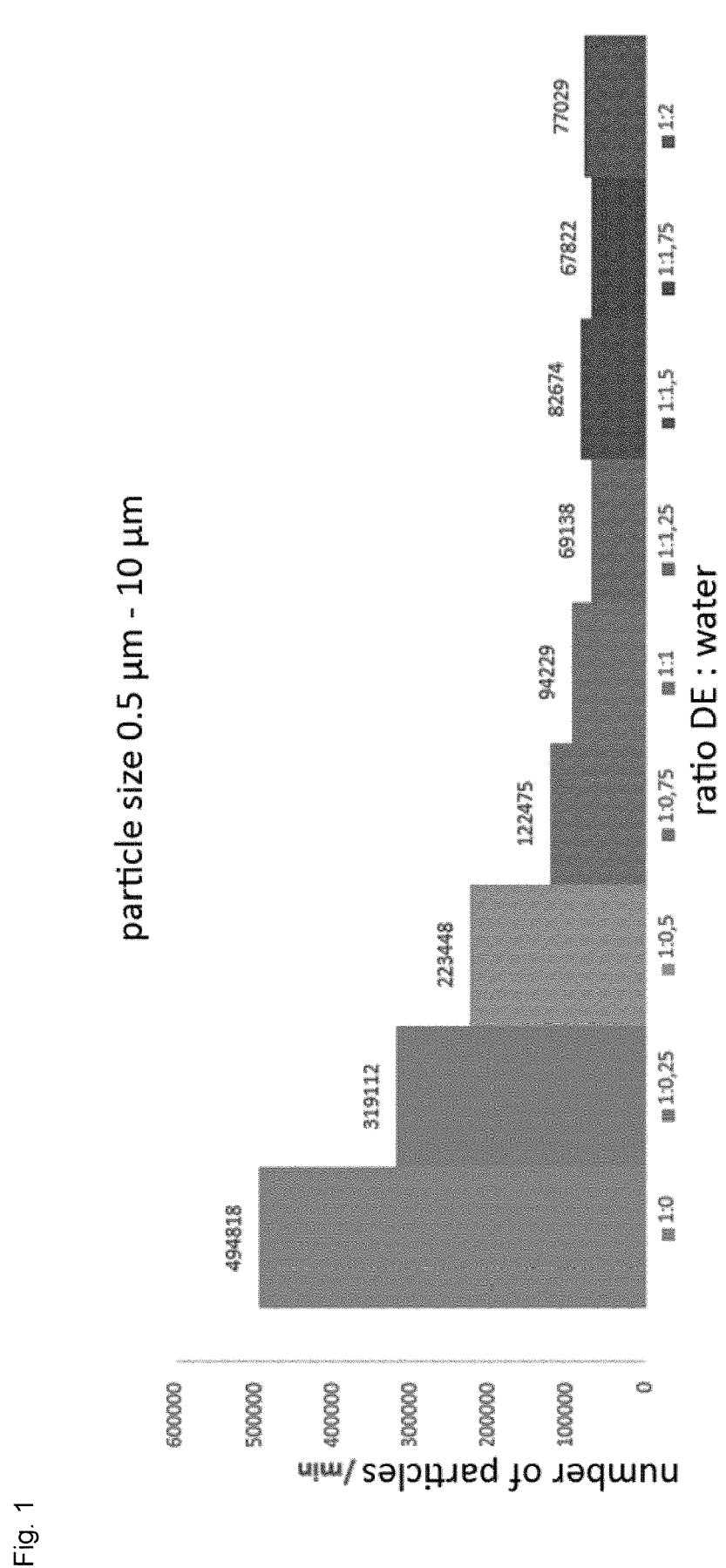
FIG. 1 shows the particle count rate (number of particles/min) as measured for different mass ratios of the calcined diatomaceous earth particles and water.
Figure 2:
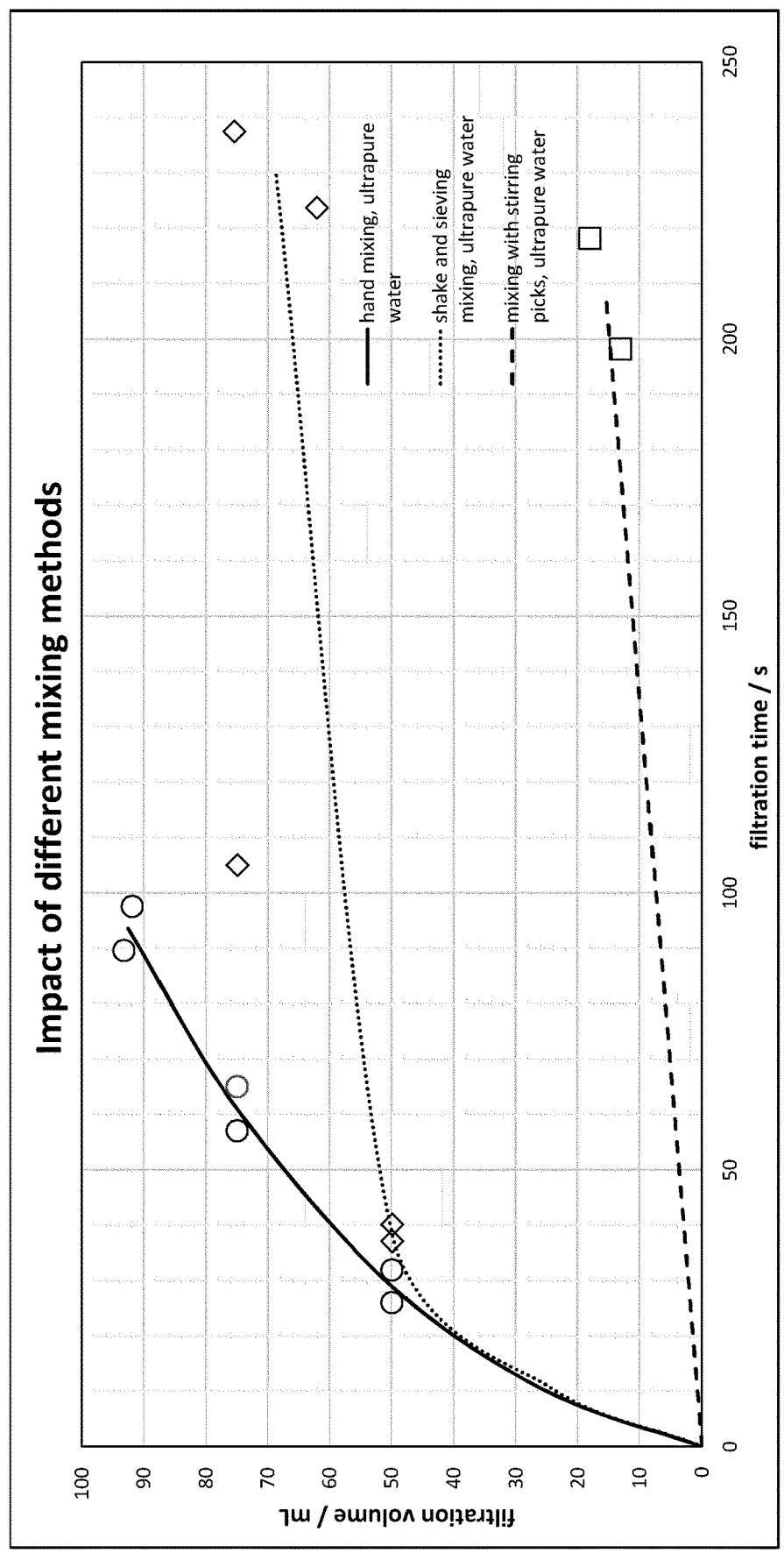
FIG. 2 shows the relationship between filtration volume and filtration time for three different mixing methods, using ultrapure water for wetting dry diatomaceous earth in each case.

In FIG. 2, there is shown the relationship between filtration volume and filtration time for three different mixing methods (hand mixing, shake and sieving mixing as well as mixing with stirring picks), using ultrapure water (Ariume® water) for wetting dry diatomaceous earth in each case. The mixing methods differed in their intensity, which means that the shear forces occurring during the mixing process were different. As can be seen from FIG. 2, mixing method 1 (hand mixing) which induced the least shear forces resulted in the best filtration performance, i.e. a high filtration volume at a low filtration time, while mixing method 3 (mixing with stirring picks) which induced the most shear forces resulted in the worst filtration performance, i.e. a low filtration volume at a high filtration time, among the three mixing methods applied herein. For each mixing method, FIG. 2 shows best-fit curves which are based on two separate data sets, respectively.

Specifically, the three mixing methods applied herein were as follows:

Mixing Method 1 (Hand Mixing)

For hand mixing, the respective amounts of the calcined diatomaceous earth particles and the wetting medium were brought together in a vessel. Hand mixing was then conducted with a spatula to crush chunks of the wetted diatomaceous earth particles and to mix them with each other. Hand mixing was completed when the obtained diatomaceous earth composition appeared homogenous.

Mixing Method 2 (Shake and Sieving Mixing)

For shake and sieving mixing, the respective amounts of the calcined diatomaceous earth particles and the wetting medium were brought together in a vessel. The vessel was closed and shaken for one minute to coarsely mix the diatomaceous earth particles and the wetting medium. After that, the vessel was opened and the contents thereof were placed on a sieve. Depending on their size, the contents either directly passed the sieve or rubbing had to be applied to get the contents passed therethrough. The sieved contents were collected and slightly stirred to obtain a diatomaceous earth composition which appeared homogeneous.

Mixing Method 3 (Mixing with Stirring Picks)

For mixing with stirring picks, the respective amounts of the calcined diatomaceous earth particles and the wetting medium were brought together in a vessel. Mixing was conducted with the stirring picks operating at the highest power level for five minutes, thereby obtaining a diatomaceous earth composition which appeared homogenous.

Figure 3:
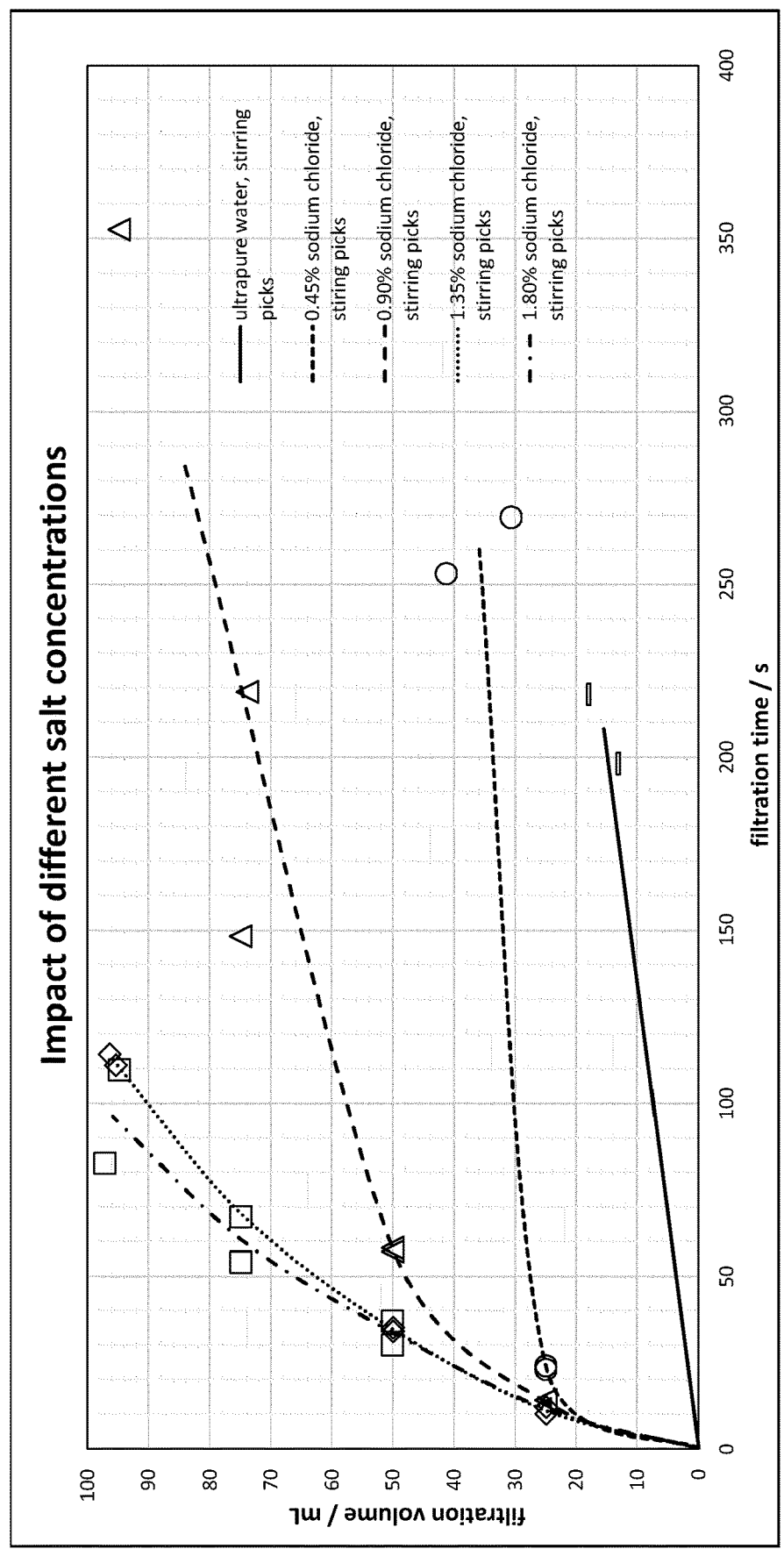
FIG. 3 shows the relationship between filtration volume and filtration time for one of said three mixing methods, using ultrapure water as well as solutions of sodium chloride with different amounts in ultrapure water for wetting dry diatomaceous earth.

In FIG. 3, there is shown the relationship between filtration volume and filtration time for mixing method 3 (mixing with stirring picks), using ultrapure water (Ariume® water) as well as solutions of sodium chloride with different amounts in ultrapure water for wetting dry diatomaceous earth. As can be seen from FIG. 3, the filtration performance increased when the wetting medium contained an increasing amount of sodium chloride. For each wetting medium, FIG. 3 shows best-fit curves which are based on two separate data sets, respectively.

Figure 4:
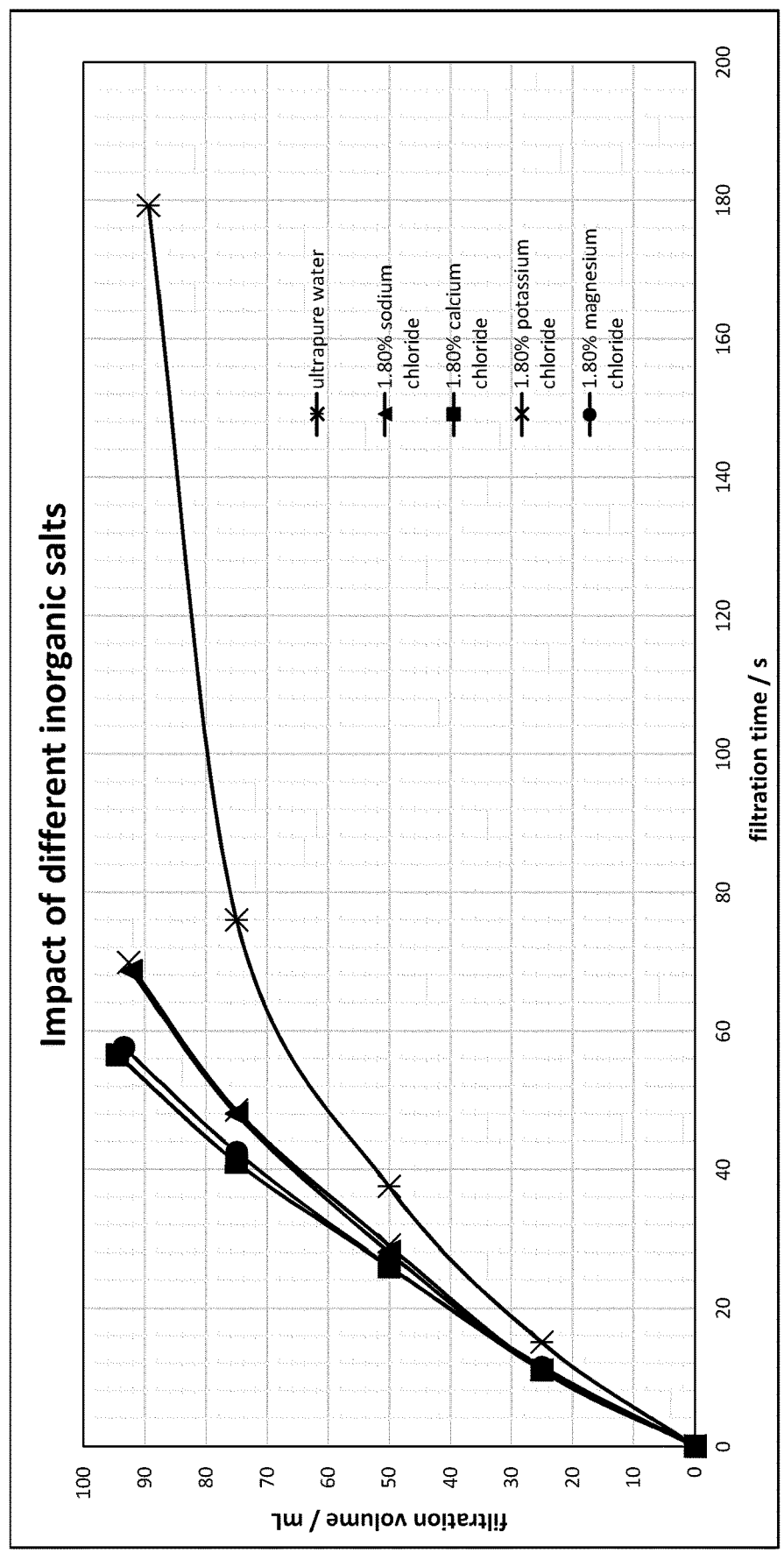
FIG. 4 shows the relationship between filtration volume and filtration time for one of said three mixing methods, using ultrapure water as well as solutions of different inorganic salts with constant amounts in ultrapure water for wetting dry diatomaceous earth.

In FIG. 4, there is shown the relationship between filtration volume and filtration time for mixing method 2 (shake and sieving mixing), using ultrapure water (Ariume® water) as well as solutions of different inorganic salts with constant amounts in ultrapure water for wetting dry diatomaceous earth. As can be seen from FIG. 4, using aqueous solutions of sodium chloride, potassium chloride, magnesium chloride and calcium chloride resulted in an increased filtration performance compared to ultrapure water as the wetting medium.

By means of elemental analysis, it was found that ultrapure water dispersed diatomaceous earth to a small extent, eluting silicon in form of silica, as can be taken from Table 1 below.

TABLE 1

| sample | searched element [mg/L] | | | | |
|---|---|---|---|---|---|
| | aluminum | lead | boron | silicon | silica as $SiO_2$ |
| arium ® water | 0.08 | <0.001 | 0.16 | 7.2 | 15 |
| 0.9% NaCl | <0.02 | <0.001 | 0.12 | 2.8 | 6.0 |
| 2.0% NaCl | <0.02 | <0.001 | 0.19 | 2.6 | 5.6 |

The values shown in Table 1 were determined by ICP (inductively coupled plasma) measurement. Herein, as well as in the Figures, the values given in "%" mean "mass %". That is, 0.9% NaCl correspond to 0.9 parts by mass of NaCl based on (100-0.9) parts by mass of water (i.e. 0.908 parts by mass of NaCl based on 100 parts by mass of water), and 2.0% NaCl correspond to 2.0 parts by mass of NaCl based on (100-2.0) parts by mass of water (i.e. 2.04 parts by mass of NaCl based on 100 parts by mass of water).

Even though the amount of eluted silica may be seen as comparatively small when using ultrapure water, it considerably reduced the mechanical strength of the diatomaceous earth particles towards shear forces, altering the surface characteristics thereof. As a result, the filtration performance was deteriorated, as expressed by the relationship between filtration volume and filtration time.

On the other hand, it has been found by the present inventors that the amount of eluted silica can be significantly reduced when a solution of an inorganic salt in water, such as an aqueous solution of sodium chloride, is used for wetting the calcined diatomaceous earth particles, as can be taken from Table 1 above. In contrast to using ultrapure water, the calcined diatomaceous earth particles then maintain their mechanical strength towards shear forces, and the surface characteristics thereof are not substantially altered. As a result, excellent filtration performance is maintained.

The diatomaceous earth composition according to the present invention shows a reduced release of dust particles, and at the same time, maintains excellent filtration performance. As such, it may be suitably used as an agent for precoat filtration or dynamic body feed filtration in biopharmaceutical applications, in particular for precoat filtration or dynamic body feed filtration of eukaryotic and/or prokaryotic cells in an aqueous medium.

The invention claimed is:

1. A diatomaceous earth composition, comprising an agglomerated mixture of calcined diatomaceous earth particles, water and at least one inorganic salt, and further comprising a water-impermeable and γ-sterilizable packaging sealing the agglomerated mixture of calcined diatomaceous earth particles, water and at least one inorganic salt;
   wherein the mass ratio of the calcined diatomaceous earth particles and water is in the range of 1:1.0 to 1:2.0, and
   wherein the content of the at least one inorganic salt is equal to or more than 0.25 parts by mass based on 100 parts by mass of water, and
   wherein the diatomaceous earth composition has an endotoxin content of equal to or less than 0.5 EU/mL;
   wherein the water-impermeable and γ-sterilizable packaging is composed of a four-layered laminate comprising the following layers (i) to (iv) from the inside to the outside of the packaging:
   (i) a layer of polyethylene or polypropylene having a thickness in the range of 30 to 150 μm;
   (ii) a layer of polyethylene terephthalate or oriented polyamide having a thickness in the range of 5 to 20 μm;
   (iii) a layer of aluminum having a thickness in the range of 5 to 20 μm; and
   (iv) a layer of polyethylene terephthalate having a thickness in the range of 5 to 20 μm.

2. The diatomaceous earth composition according to claim 1, wherein the mass ratio of the calcined diatomaceous earth particles and water is in the range of 1:1.1 to 1:1.7.

3. The diatomaceous earth composition according to claim 2, wherein the mass ratio of the calcined diatomaceous earth particles and water is in the range of 1:1.2 to 1:1.4.

4. The diatomaceous earth composition according to claim 1, wherein the content of the at least one inorganic salt is equal to or more than 0.5 parts by mass based on 100 parts by mass of water.

5. The diatomaceous earth composition according to claim 1, wherein the at least one inorganic salt is selected from an alkali metal halide, an alkaline earth metal halide, or mixtures thereof.

6. The diatomaceous earth composition according to claim 5, wherein the at least one inorganic salt is selected from the group consisting of sodium chloride, potassium chloride, magnesium chloride and calcium chloride.

7. The diatomaceous earth composition according to claim 1, wherein the average particle size of the calcined diatomaceous earth particles is in the range of 0.5 to 10 μm.

8. A method for producing the diatomaceous earth composition according to claim 1, comprising the following steps:

(a) providing calcined diatomaceous earth particles and a solution of at least one inorganic salt in water, wherein the content of the at least one inorganic salt is equal to or more than 0.25 parts by mass based on 100 parts by mass of water;

(b) mixing the calcined diatomaceous earth particles with the solution of at least one inorganic salt in water, wherein the mass ratio of the calcined diatomaceous earth particles and water is in the range of 1:1.0 to 1:2.0, thereby obtaining an agglomerated mixture of calcined diatomaceous earth particles, water and at least one inorganic salt;

(c) sealing the agglomerated mixture of calcined diatomaceous earth particles, water and at least one inorganic salt obtained in step (b) in the water-impermeable and γ-sterilizable packaging, thereby obtaining a sealed agglomerated mixture of calcined diatomaceous earth particles, water and at least one inorganic salt;

(d) optionally sterilizing the sealed agglomerated mixture of calcined diatomaceous earth particles, water and at least one inorganic salt obtained in step (c) by exposure to γ-radiation, thereby obtaining a diatomaceous earth composition with an endotoxin content of equal to or less than 0.5 EU/mL; and (e) optionally removing the packaging from the diatomaceous earth composition obtained in step (c) or (d).

9. The method according to claim 8, wherein the calcined diatomaceous earth particles and the solution of at least one inorganic salt in water are mixed in step (b) by spray wetting.

10. The method according to claim 8, wherein the γ-radiation for sterilizing the sealed agglomerated mixture of calcined diatomaceous earth particles, water and at least one inorganic salt in step (d) has a dose in the range of 25 to 100 kGy.

11. A method of purifying a supernatant, comprising adding a diatomaceous earth composition according to claim 1 to the supernatant, and performing precoat filtration or dynamic body feed filtration using the supernatant comprising the diatomaceous earth composition.

12. The method according to claim 11 wherein the supernatant comprises eukaryotic and/or prokaryotic cells in an aqueous medium.

* * * * *